(12) United States Patent
Zhu et al.

(10) Patent No.: US 10,221,145 B2
(45) Date of Patent: Mar. 5, 2019

(54) METHOD FOR PREPARING ANTI-HEART-FAILURE MEDICINE LCZ696

(71) Applicant: ZHEJIANG TIANYU PHARMACEUTICAL CO., LTD., Taizhou, Zhejiang (CN)

(72) Inventors: Guorong Zhu, Zhejiang (CN); Yongjun Tu, Zhejiang (CN); Wenlong Xie, Zhejiang (CN); Zhen Wang, Zhejiang (CN); Shaojun Xu, Zhejiang (CN)

(73) Assignee: ZHEJIANG TIANYU PHARMACEUTICAL CO., LTD., Taizhou, Zhejiang (CN)

( * ) Notice: Subject to any disclaimer, the term of this patent is extended or adjusted under 35 U.S.C. 154(b) by 0 days.

(21) Appl. No.: 16/060,297

(22) PCT Filed: Jun. 6, 2016

(86) PCT No.: PCT/CN2016/084914
§ 371 (c)(1),
(2) Date: Jun. 7, 2018

(87) PCT Pub. No.: WO2017/096772
PCT Pub. Date: Jun. 15, 2017

(65) Prior Publication Data
US 2018/0354915 A1    Dec. 13, 2018

(30) Foreign Application Priority Data
Dec. 9, 2015 (CN) .......................... 2015 1 0903519

(51) Int. Cl.
*C07D 257/02* (2006.01)
*B01D 9/00* (2006.01)
*A61P 9/12* (2006.01)

(52) U.S. Cl.
CPC ......... *C07D 257/02* (2013.01); *B01D 9/0054* (2013.01); *B01D 9/0063* (2013.01); *A61P 9/12* (2018.01)

(58) Field of Classification Search
CPC ........................... C07D 257/02; B01D 9/0054
See application file for complete search history.

(56) References Cited

U.S. PATENT DOCUMENTS

2016/0206597 A1    7/2016    Bransford et al.

FOREIGN PATENT DOCUMENTS

| CN | 102091330 A | 6/2011 |
|---|---|---|
| CN | 101098689 B | 2/2013 |
| CN | 105348209 A | 2/2016 |
| CN | 104860894 B | 5/2017 |
| KR | 20100057704 A | 5/2010 |
| RU | 2503668 C2 | 1/2014 |
| WO | 03059345 A1 | 7/2003 |
| WO | 2006086456 A2 | 8/2006 |
| WO | 2007045663 A2 | 4/2007 |
| WO | 2007056546 A1 | 5/2007 |
| WO | 2008031567 A1 | 3/2008 |
| WO | 2008083967 A2 | 7/2008 |
| WO | 2010034236 A1 | 4/2010 |
| WO | 2014032627 A1 | 3/2014 |
| WO | 2015030711 A1 | 3/2015 |

OTHER PUBLICATIONS

Qihan Zhang et al., "Organic Chemistry Laboratory Experiments(Third Edition)", pp. 38-39, Jun. 2015, Beijing, China.
Lili Feng et al., "LCZ696: a dual-acting sodium supramolecular complex", Tetrahedron Letters, vol. 53, 2012, pp. 278-276.

*Primary Examiner* — Golam M Shameem
(74) *Attorney, Agent, or Firm* — Novick, Kim & Lee, PLLC; Allen Xue (57) ABSTRACT

The present invention discloses a method for preparing an anti-heart-failure medicine LCZ696. The preparing method comprises the following step (formula (I)): in an organic solvent, a Sacubitril dicyclohexylamine salt reacts with valsartan under the effect of a sodium hydroxide aqueous solution, and the anti-heart-failure medicine LCZ696 is obtained. The preparing method of the present invention is simple in process and omits the procedures of ion exchange from a sodium salt to a calcium salt and hydrochloric acid dissociation in an existing production process, residues of calcium ions are avoided, and the production efficiency is effectively improved.

16 Claims, 6 Drawing Sheets

METHOD FOR PREPARING ANTI-HEART-FAILURE MEDICINE LCZ696

TECHNICAL FIELD

The present invention relates to the field of pharmaceutical synthesis, and in particular to a method for preparing an anti-heart-failure dr LCZ696.

BACKGROUND

LCZ696 is a novel antihypertensive anti-heart-failure drug developed by Novartis. It is a sacubitril/valsartan complex. The medicine mainly contains two components: Diovan (common name: valsartan) of Novartis and experimental medicine Sacubitril (AHU-377), wherein the Sacubitril can block an action mechanism which threatens two polypeptides in charge of reducing the blood pressure, and the medicine was approved by U.S. Food and Drug Administration on 7 Jul., 2015, and is used for the heart failure patients with a reduced ejection fraction, to reduce the cardiovascular death and heart failure hospitalization risks. The LCZ696 is generally obtained by subjecting Diovan and Sacubitril with a molar ratio of 1:1 to cocrystallization in the mixed solvent of a sodium hydroxide aqueous solution and an organic solvent. LCZ696 consists of Diovan:Sacubitril:Na:H$_2$O=1:1:3:2.5 (molar ratio), and has a chemical formula is as shown in the following formula I.

Formula I

The Sacubitril gains wide attention as an important constituent of LCZ696. The chemical name of the Sacubitril is 4-{[(2S,4R)-1-(4-biphenylyl)-5-ethoxy-4-methyl-5-oxo-2-pentanyl]amino}-4-oxobutanoic acid, with a Chinese name of: (4-{[(2S,4R)-1-(4-联苯基)-5-乙氧基-4-甲基-5-氧代-2-戊基]氨基}-4-氧代丁酸), and its chemical formula is as shown in the following formula II:

Formula II

At present, there are many reports about synthetic methods for Sacubitril, for example, patents WO2008083967, WO2008031567, WO2008031567, WO2010034236, WO2014032627 or the like. Although the synthetic methods for the Sacubitril are relatively mature, due to the influence of the long chain alkyls in molecular structures per se, the crude product of the Sacubitril in the large scale production process is colorless viscous liquid, as a result, the problems that the Sacubitril is hard to be purified and the quality is hard to be controlled are caused.

In the other aspect, in the production process for LCZ696 reported by patent WO2007056546 to Novartis, the crude product of Sacubitril reacts with sodium hydroxide at first to form a sodium salt, then the sodium salt is converted to a calcium salt by ion exchange with calcium chloride to form an isolated solid, the obtained solid is dissociated again with diluted hydrochloric acid, and free acid is regained after the procedures of extraction and concentration. Afterwards, the free Sacubitril acid and valsartan are dissolved in an organic solvent, and the obtained mixture and a sodium hydroxide aqueous solution are subjected to a salt forming reaction and a cocrystallization process to obtain LCZ696. The whole production process needs repeated dissociation and ion exchange, thereby causing a relatively tedious production process flow and the residues of calcium ions which are hard to control.

In addition, patents WO03059345, WO2006086456 and WO2007045663 applied by Novartis discloses the triethanolamine salt and tromethamine salt of Sacubitril. The organic amine salts of the Sacubitril disclosed in these patents are directly used for forming pharmaceutical composition with the valsartan, without preparing LCZ696 by cocrystallization of these organic amine salts after reacting with the valsartan and sodium hydroxide.

SUMMARY

The technical problem to be solved by the present invention is to provide a method for preparing anti-heart-failure drug LCZ696 in view of the above defects in the prior art. The process according to the present invention is simple, and avoids the procedures of ion exchange from a sodium salt to a calcium salt and hydrochloric acid dissociation in an existing production process, the residues of calcium ions are avoided, and the production efficiency is effectively improved.

The present invention provides a method for preparing LCZ696, comprising the following steps: in an organic solvent, reacting a Sacubitril dicyclohexylamine salt with valsartan under the effect of a sodium hydroxide aqueous solution, thereby obtaining LCZ696:

sacubitril dicyclohexylamine salt valsarta

Herein, the organic solvent may be various organic solvents conventionally used in the art, and is preferably a mixed solvent of isopropyl acetate and acetone or a mixed solvent of isopropyl acetate and acetonitrile or acetonitrile.

Herein, the molar ratio of the Sacubitril dicyclohexylamine salt to the valsartan is preferably 1:0.95-1.10, and more preferably 1:1.05.

Herein, the molar ratio of the Sacubitril dicyclohexylamine salt to Sodium hydroxide is preferably 1:2.95-3.10, and more preferably 1:3.05.

Herein, the mass percent concentration of the sodium hydroxide aqueous solution is preferably 30%-40%.

Herein, the preparing method preferably comprises the following steps: dissolving the Sacubitril dicyclohexylamine salt in the organic solvent, adding the valsartan after the obtained solution is clear by raising temperature and through dissolving process, then adding the sodium hydroxide aqueous solution dropwise, and then performing crystallization.

Herein, the temperature for the process that the obtained solution is clear by raising temperature and through dissolving process is preferably 50-65° C.

Herein, after the sodium hydroxide aqueous solution is added dropwise and before the crystallization, when the organic solvent is the mixed solvent of isopropyl acetate and acetone or the mixed solvent of isopropyl acetate and acetonitrile, the operation step (i) is preferred: adding the isopropyl acetate dropwise and performing reduced pressure distillation; and repeating the operation step (i) for 2-3 times; the operation step (ii) is more preferred: adding the isopropyl acetate dropwise within a temperature range of 40±3° C., performing temperature preservation at 40±3° C., performing reduced pressure distillation in a temperature range of 35±5° C.; and repeating the operation step (ii) for 2-3 times.

Herein, after the sodium hydroxide aqueous solution is added dropwise and before the crystallization, when the organic solvent is acetonitrile, the temperature preservation is preferably performed at 50-55° C.

The time for the temperature preservation at 40±3° C. is preferably 0.5-1 h.

The crystallization temperature is preferably 0-60° C., and more preferably 20-25° C.

After the crystallization is finished, a conventional post-processing step can be further performed to obtain the LCZ 696 according to the present invention. The post-processing step is preferably filtration and reducing pressure drying.

In the present invention, the Sacubitril dicyclohexylamine salt may be made by the following process: reacting Sacubitril with dicyclohexylamine in ethyl acetate.

The method for preparing the Sacubitril dicyclohexylamine salt preferably comprises the following steps: dissolving the Sacubitril in the ethyl acetate at 10-30° C., adding the dicyclohexylamine dropwise, and precipitating a solid by slowly cooling to 0-5° C. under a stirring condition.

Herein, the molar ratio of the Sacubitril to the dicyclohexylamine is preferably 1:1.0-1.2, and more preferably 1:1.05.

Herein, the slow cooling is preferably natural cooling.

The present invention provides a Sacubitril dicyclohexylamine salt, and its structure is as shown in the following formula III, Formula III The present invention further provides the crystal form of the Sacubitril dicyclohexylamine salt, and when the diffractive angle of the X-ray powder diffraction for the crystal form is 2θ, the characteristic diffraction peaks are 6.6°±0.2°, 7.2°±0.2°, 8.3°±0.2°, 9.7°±0.2°, 13.0°±0.2°, 14.5°±0.2°, 15.5°±0.2°, 16.6°±0.2°, 17.0°±0.2°, 18.0°±0.2°, 19.4°±0.2°, 19.9°±0.2°, 20.8°±0.2°, 22.4°±0.2°, 25.0°±0.2°, 25.9°±0.2° and 26.3°±0.2°; and the target form used in the X-ray powder diffraction is a Cu target.

The melting point of the crystal form is 121-123° C., and a DSC peak value is preferably 122.23° C.

The present invention further provides a method for preparing the above Sacubitril dicyclohexylamine salt, which comprises the following step: reacting Sacubitril with dicyclohexylamine in ethyl acetate.

The preparing method preferably comprises the following steps: dissolving the Sacubitril in the ethyl acetate at 10-30° C., adding the dicyclohexylamine dropwise, and precipitating a solid by slowly cooling to 0-5° C. under a stirring condition.

Herein, the molar ratio of the Sacubitril to the dicyclohexylamine is preferably 1:1.0-1.2, and more preferably 1:1.05.

Herein, the slow cooling is preferably natural cooling.

The present invention further provides a method for preparing the above crystal form of the Sacubitril dicyclohexylamine salt, which comprises the following steps: adding the Sacubitril dicyclohexylamine salt into an organic solvent, heating the obtained solution under a refluxing condition till the salt is dissolved, and performing crystallization by slowly cooling to 0-5° C. after stirring.

Herein, the organic solvent may be various organic solvents conventionally used in the art, and is preferably one or more of methanol, ethyl alcohol, isopropyl alcohol, ethyl acetate, isopropyl acetate, methylbenzene and acetone.

Herein, the ratio of mass to volume of the Sacubitril dicyclohexylamine salt to the organic solvent is preferably 1:2-20 g/mL, more preferably 1:4-10 g/mL and most preferably 1:5 g/mL.

Herein, the slow cooling is preferably natural cooling.

After the crystallization is finished, a conventional post-processing step can be performed to obtain the crystal form of the Sacubitril dicyclohexylamine salt according to the present invention. The post-processing step is preferably filtration and vacuum drying.

The present invention has the following beneficial effects.

(1) The inventive process for preparing LCZ696 is simple and easy to handle, with omission of the procedures of ion exchange from the sodium salt to the calcium salt and hydrochloric acid dissociation in the production process of Novartis, and effective improvement of production efficiency.

(2) By the inventive process for preparing LCZ696, the crystal form of the Sacubitril dicyclohexylamine salt is stable and suitable for long-term storage and transportation.

(3) In the inventive process for preparing LCZ696, no residues of calcium ions is present.

DETAILED DESCRIPTION

The present invention will be further described through specific examples, but the present invention is not limited in the scope of the examples. The experimental methods without clearly-indicated specific conditions in the following embodiments are selected according to the conventional methods and conditions or the specification of commodities.

EXAMPLE 1

Preparation of the Crude Product of Sacubitril Dicyclohexylamine Salt

Under room temperature (10-30° C.), 4.5 g Sacubitril is added into 25 ml ethyl acetate, after the solution is clear by stirring, 1.7 g dicyclohexylamine is slowly added dropwise, the stirring is continued to precipitate a solid, afterwards, natural cooling is performed to 3° C., at which temperature preservation is performed for 2 h, then filtering is performed, the filter cake is washed with the ethyl acetate, and vacuum drying is performed to obtain 6.0 g white powder, i.e., the crude product of the Sacubitril dicyclohexylamine salt.

EXAMPLE 2

Preparation of the Crystal Form of the Sacubitril Dicyclohexylamine Salt 6.0 g crude product of the Sacubitril dicyclohexylamine salt made in Embodiment 1 is added into 50 ml ethyl acetate, heated to 78° C. for dissolving, and stirred for half hour, then the obtained solution is subjected to natural cooling to 2° C. for performing crystallization, and the solution is filtered, and is subjected to vacuum drying to obtain 5.6 g white crystal, with a yield of 93%, and a melting point of 122-123° C. The DSC diagram of the obtained crystal (crystal form I) refers to FIG. 1, and the powder X-ray diffraction spectrum thereof refers to FIG. 2.

Figure 3:
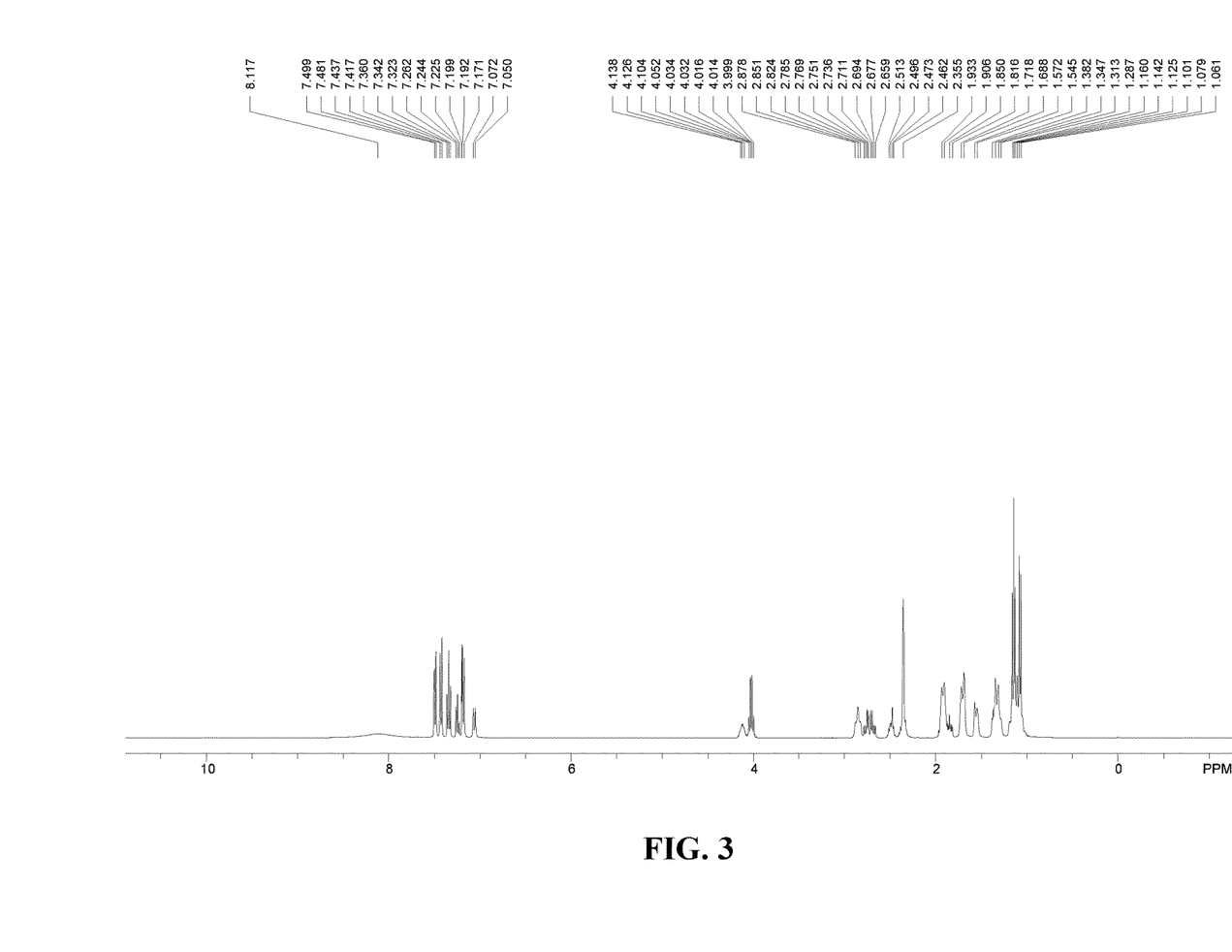
FIG. 3 is a $^1$HNMR diagram for the Sacubitril dicyclohexylamine salt prepared by an embodiment of the present invention.
Figure 4:
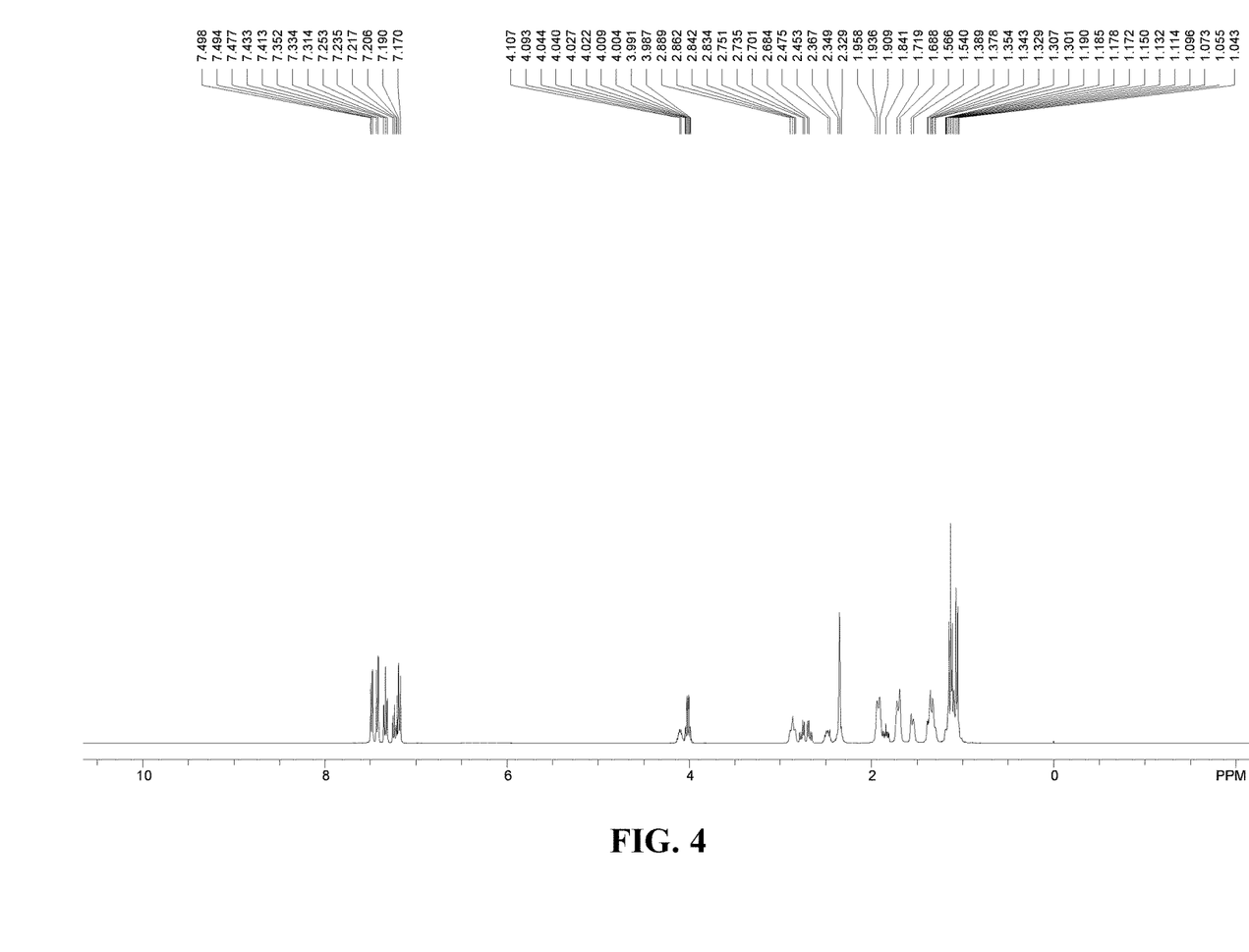
FIG. 4 is a $^1$HNMR diagram after heavy water exchange for the Sacubitril dicyclohexylamine salt prepared by an embodiment of the present invention.
Figure 5:
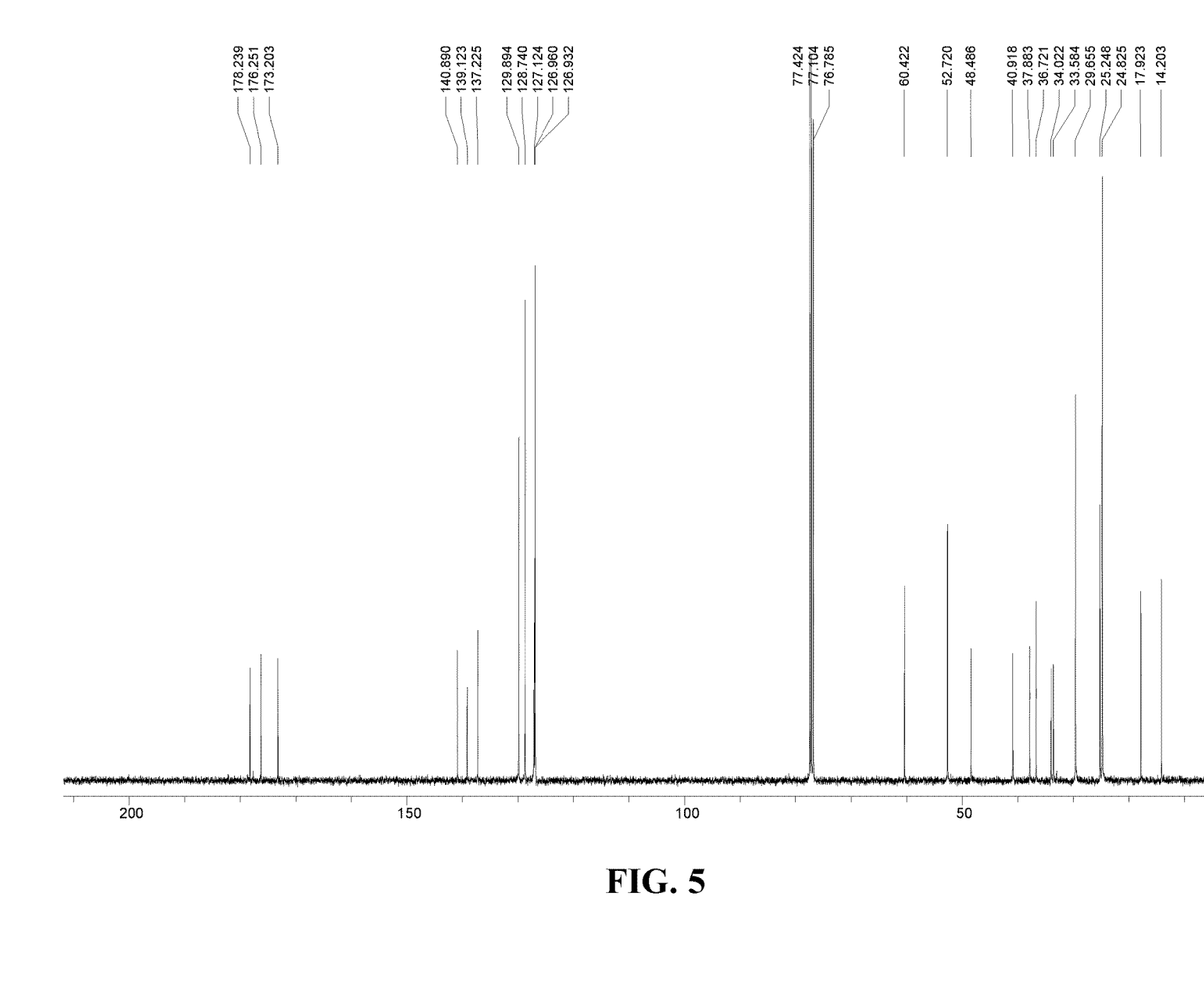
FIG. 5 is a $^{13}$CNMR diagram for the Sacubitril dicyclohexylamine salt prepared by an embodiment of the present invention.

The $^1$HNMR diagram for the Sacubitril dicyclohexylamine salt is as shown in FIG. 3; the $^1$HNMR diagram of the Sacubitril dicyclohexylamine salt after deuteroxideexchange is as shown in FIG. 4; and the $^{13}$CNMR diagram of the Sacubitril dicyclohexylamine salt is as shown in FIG. 5.

The nuclear magnetic data is as follows: $^1$HNMR (400 MHz, CDCl$_3$): δ 8.70 (br, 2H), 7.49 (m, 2H), 7.41 (m, 2H), 7.37 (m, 1H), 7.25-7.10 (m, 2H), 4.05 (br, 1H), 4.01 (m, 2H), 2.86 (m, 2H), 2.70 (m, 2H), 2.47 (m, 2H), 2.36 (m, 4H), 1.93 (m, 5H), 1.68 (m, 4H), 1.52 (m, 2H), 1.36 (m, 5H), 1.10 (m, 12H); $^{13}$C NMR (100 MHz, CDCl$_3$): 178.24, 176.25, 173.20, 140.89, 139.12, 137.23, 129.89, 128.74, 127.12, 126.96, 126.93, 60.42, 52.72, 48.49, 40.92, 37.88, 36.72, 34.02, 33.58, 29.66, 25.25, 24.83, 17.92, 14.20 ppm.

Figure 6:
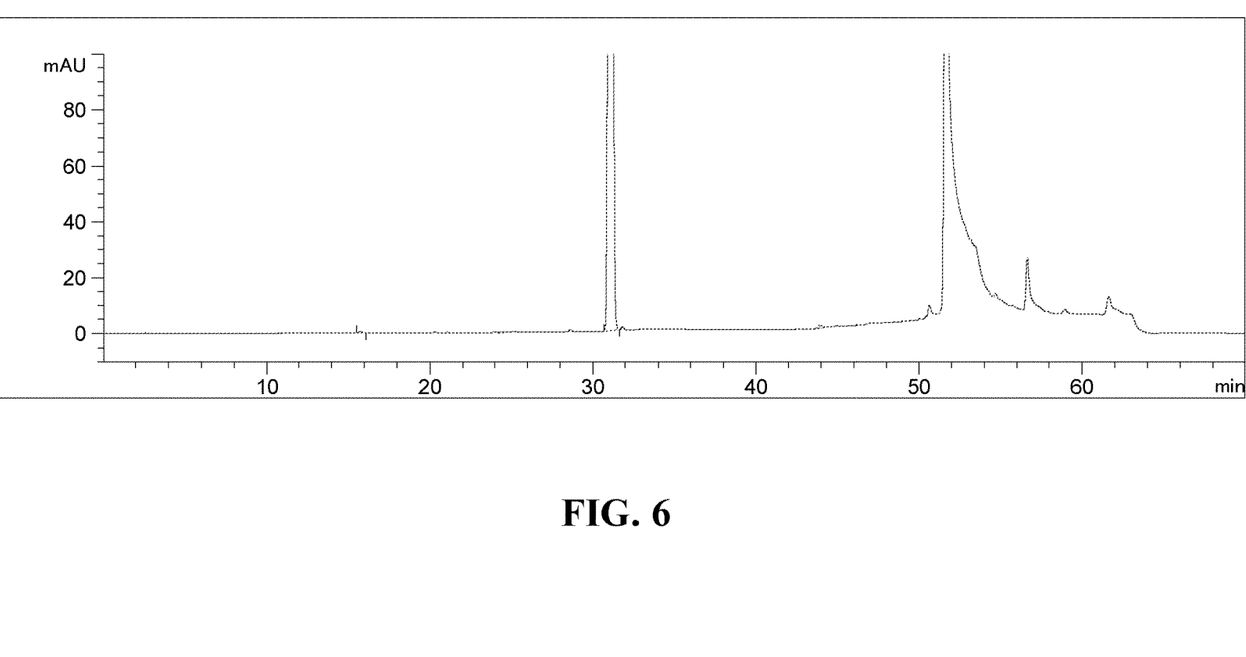
FIG. 6 is an HPLC diagram for the Sacubitril dicyclohexylamine salt prepared by an embodiment of the present invention.

The HPLC diagram for the Sacubitril dicyclohexylamine salt is as shown in FIG. 6, and data for respective peaks in the figure is as shown in the following table.

| Peak Number | Time (min) | Peak Width (min) | Peak Height (mAU) | Area (%) |
| --- | --- | --- | --- | --- |
| 1 | 15.770 | 0.1750 | 5.63530e-1 | 0.0458 |
| 2 | 31.098 | 0.2224 | 989.22791 | 99.8636 |
| 3 | 43.942 | 0.1980 | 1.02434 | 0.0907 |

EXAMPLES 3-8

Figure 1:
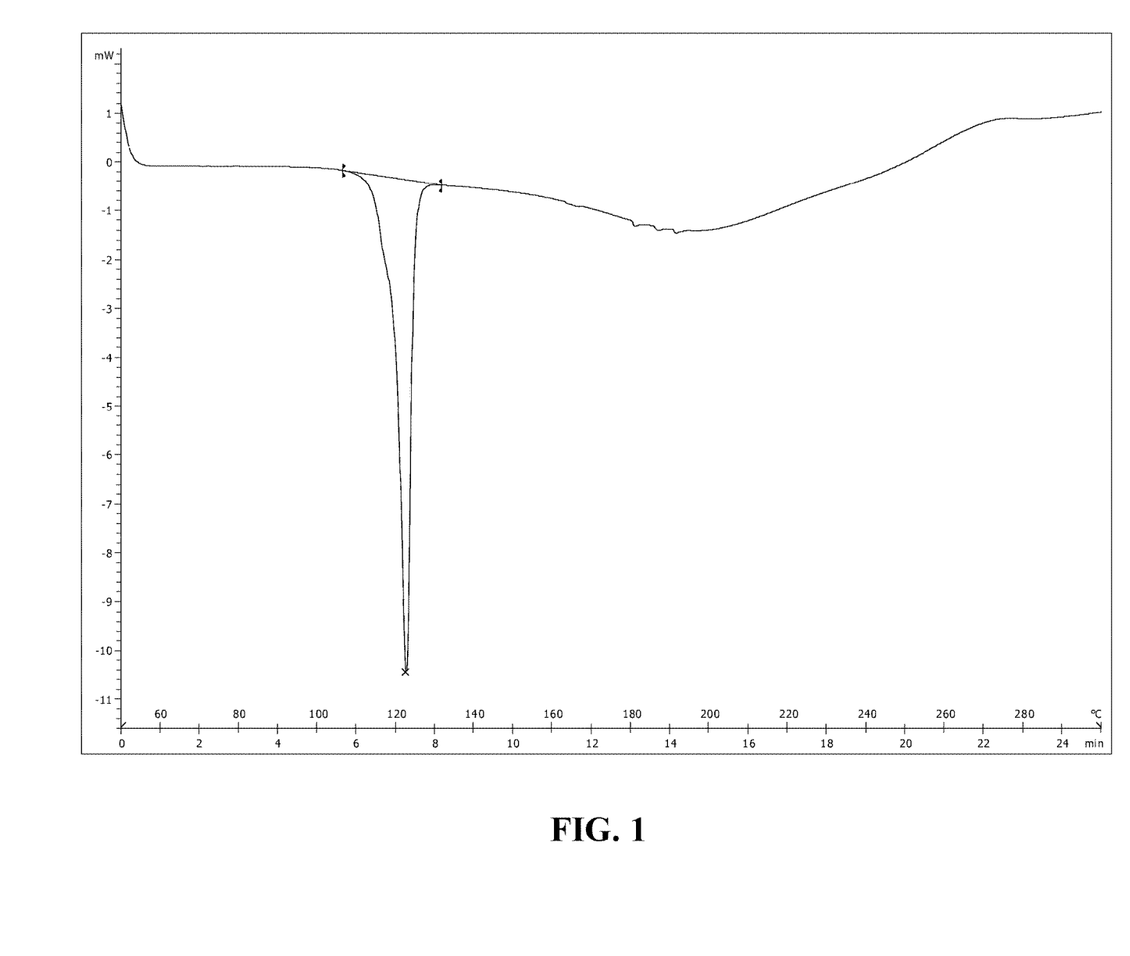
FIG. 1 is a DSC diagram for the Sacubitril dicyclohexylamine salt prepared by an embodiment of the present invention.
Figure 2:
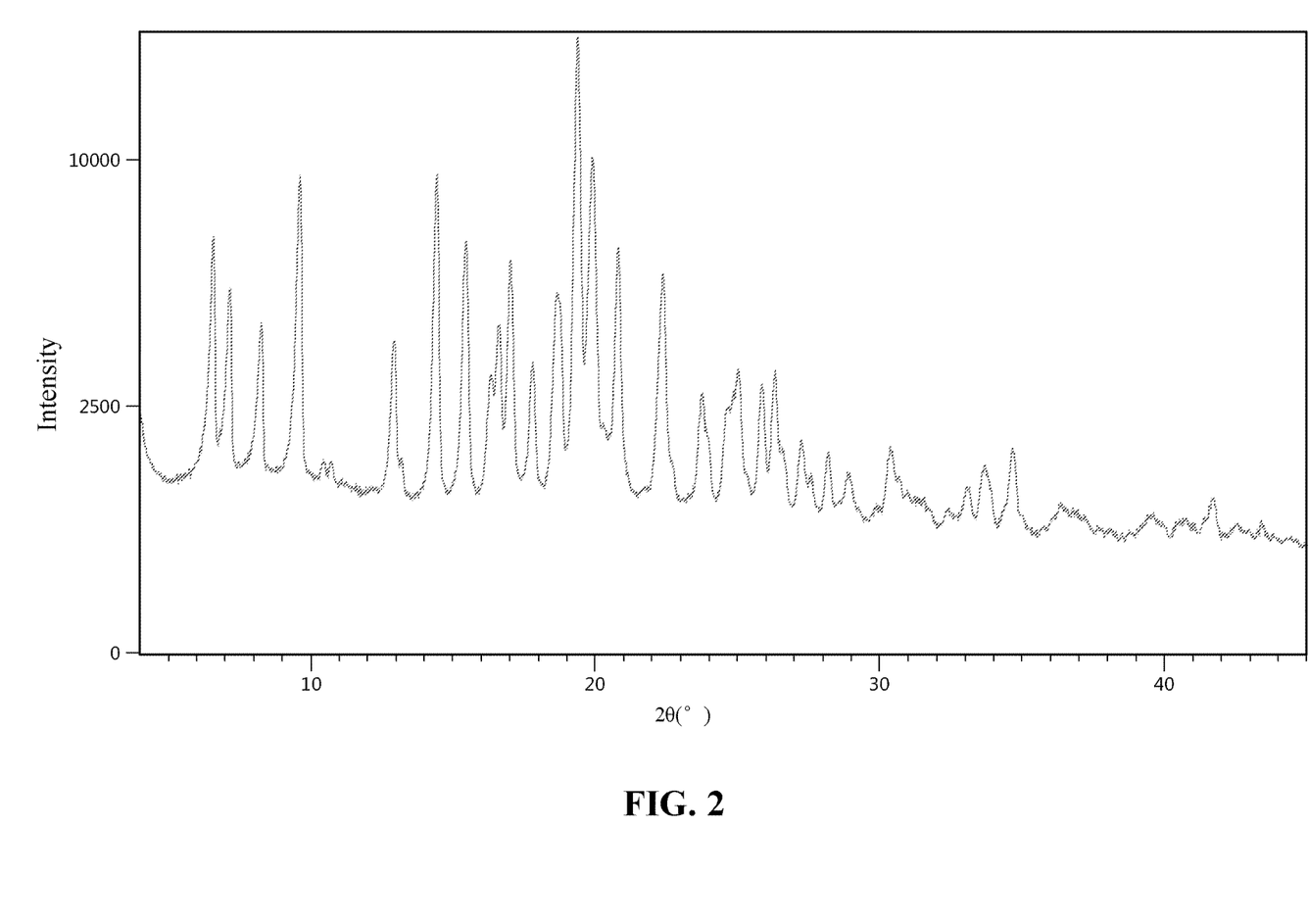
FIG. 2 is a powder X-ray diffractive diagram for the Sacubitril dicyclohexylamine salt prepared by an embodiment of the present invention.

According to the operation process of Embodiment 2, crystallization is performed by using varying different solvents, usage amounts and temperature conditions, see the embodiments in the following table for results, the DSC diagram for the obtained crystal form is seen in FIG. 1, the powder X-ray diffraction spectrum thereof is seen in FIG. 2, nuclear magnetic data is the same as that in Embodiment 2, and HPLC spectrum is as shown in FIG. 6.

| Number | Usage Amount of Dicyclohexylamine Salt | Solvent for Crystallization | Usage Amount of Solvent | Heating Temperature | Temperature for Crystallization | Yield | Crystal Form |
|---|---|---|---|---|---|---|---|
| Embodiment 3 | 6.0 g | Methylbenzene | 70 mL | 110° C. | 1° C. | 94% | Crystal Form I |
| Embodiment 4 | 6.0 g | Isopropyl Acetate | 60 mL | 88° C. | 0° C. | 92% | Crystal Form I |
| Embodiment 5 | 6.0 g | Methanol | 30 mL | 63° C. | 5° C. | 85% | Crystal Form I |
| Embodiment 6 | 6.0 g | Ethyl Alcohol | 40 mL | 78° C. | 4° C. | 88% | Crystal Form I |
| Embodiment 7 | 6.0 g | Isopropyl Alcohol | 40 mL | 89° C. | 2° C. | 92% | Crystal Form I |
| Embodiment 8 | 6.0 g | Acetone | 50 mL | 57° C. | 3° C. | 87% | Crystal Form I |

EXAMPLE 9

Preparation of LCZ696 by the Sacubitril Dicyclohexylamine Salt

The Sacubitril dicyclohexylamine salt (84 g, 142 mmol) is dissolved into the mixed solvent of 60 mL isopropyl acetate and 1220 mL acetone, the temperature is raised to 50-55° C., after the obtained solution is clear by stirring, the valsartan (63 g, 145 mmol) is added, then 47 g 36% Sodium hydroxide aqueous solution is added dropwise, the temperature preservation is performed for 2 h at 40-45° C., and then cooling is performed to room temperature (25-30° C.), at which the temperature preservation is performed for 2 h. The temperature is raised to 40±3° C. after the temperature preservation is ended, 610 mL isopropyl acetate is added dropwise, after that, the temperature preservation is performed at 40±3° C. for 0.5 h. After the temperature preservation is ended, and 760 mL solvent is removed by controlling temperature to be 35±5° C. and by pressure reduction. Then, the temperature is raised to 40±3° C., 920 mL isopropyl acetate is added dropwise, after that, the temperature is controlled to be 40±3° C. at which the temperature preservation is performed for 0.5 h. After the temperature preservation is ended, 1220 mL solvent is removed by controlling temperature to be 35±5° C., and by pressure reduction, then the temperature is raised to 40±3° C., 1220 mL isopropyl acetate is added dropwise, and after that, the temperature preservation is performed for 0.5 h. Then the temperature is controlled to be 35±5° C., and 1220 mL solvent is removed by pressure reduction. After removal, the temperature is reduced to 20-25° C. at which the temperature preservation is performed for 3 h. After the temperature preservation and crystallization are ended, reducing pressure filtering is performed to obtain a wet product. It is subjected to reducing pressure drying in an oven at a temperature of 35° C. for 12 h to obtain 116 g finished product of LCZ696, with a yield of 85% and a purity of 99.94%. The DSC and X-ray powder diffractive data for the obtained LCZ696 are matched with the data reported by Novartis, the crystal form is consistent with the crystal form reported by Novartis, and the content data of respective components of the obtained LCZ696 is seen in the following table.

|  | Content of Sacubitril | Content of Valsartan | Content of Sodium Ions | Water Content |
|---|---|---|---|---|
| Theoretical Value | 42.8% | 45.3% | 7.2% | 4.7% |
| Measured Value | 42.7% | 45.2% | 7.3% | 4.8% |

EXAMPLE 10

Preparation of LCZ696 by the Sacubitril Dicyclohexylamine Salt

Sacubitril dicyclohexylamine salt (84 g, 142 mmol) is dissolved into a mixed solvent of 60 mL isopropyl acetate and 1220 mL acetonitrile, the temperature is raised to 50-55° C., after the obtained solution is clear by stirring, valsartan (63 g, 145 mmol) is added, then 47 g 36% Sodium hydroxide aqueous solution is added dropwise, the temperature preservation is performed at 40-45° C. for 2 h, and then the temperature is reduced to room temperature (25-30° C.) at which temperature preservation is performed for 2 h. The temperature is raised to 40±3° C. after the temperature preservation is ended, 610 mL isopropyl acetate is added dropwise, after that, the temperature preservation is performed at 40±3° C. for 0.5 h. After the temperature preservation is ended, the temperature is controlled to be 35±5° C., and 760 mL solvent is removed by pressure reduction. After the removal is ended, the temperature is raised to 40±3° C., 920 mL isopropyl acetate is added dropwise, and after that, the temperature is controlled to be 40±3° C. at which temperature preservation is performed for 0.5 h. After the temperature preservation is ended, the temperature is controlled to be 35±5° C., and 1220 mL solvent is removed by pressure reduction, then the temperature is raised to 40±3° C., 1220 mL isopropyl acetate is added dropwise, and after that, the temperature preservation is performed for 0.5 h. Then the temperature is controlled to be 35±5° C., and 1220 mL solvent is removed by pressure reduction. After the removal, the temperature is reduced to 20-25° C. at which the temperature preservation is performed for 3 h. After the temperature preservation and crystallization are ended, reducing pressure filtering is performed to obtain a wet product. The wet product is subjected to reducing pressure drying in an oven at temperature of 35° C. for 12 h to obtain 119 g finished product of LCZ696, with a yield of 88% and a purity of 99.91%. The DSC and X-ray powder diffractive data for the obtained LCZ696 are matched with that reported by Novartis, the crystal form is consistent with that reported by Novartis, and the content data of respective components of the obtained LCZ696 is seen in the following table.

|  | Content of Sacubitril | Content of Valsartan | Content of Sodium Ions | Water Content |
|---|---|---|---|---|
| Theoretical Value | 42.8% | 45.3% | 7.2% | 4.7% |
| Measured Value | 42.7% | 45.1% | 7.3% | 4.9% |

EXAMPLE 11

Preparation of LCZ696 by the Sacubitril Dicyclohexylamine Salt

The Sacubitril dicyclohexylamine salt (84 g, 142 mmol) is dissolved into a mixed solvent of 60 mL isopropyl acetate and 1800 mL acetonitrile, the temperature is raised to 60-65° C., after the obtained solution is clear by stirring, the valsartan (63 g, 145 mmol) is added, then 47 g 36% sodium hydroxide aqueous solution is added dropwise, the temperature is raised to 40±3° C. after the temperature preservation is ended, 610 mL isopropyl acetate is added dropwise, and after that, the temperature preservation is performed at 40±3° C. for 0.5 h. After the temperature preservation is ended, the temperature is controlled to be 35±5° C., and 760 mL solvent is removed by pressure reduction. After the removal, the temperature is raised to 40±3° C., 920 mL isopropyl acetate is added dropwise, and after that, the temperature is controlled to be 40±3° C. at which the temperature preservation is performed for 0.5 h. After the temperature preservation is ended, the temperature is controlled to be 35±5° C., and 1220 mL solvent is removed by pressure reduction, then the temperature is raised to 40±3° C., 1220 mL isopropyl acetate is added dropwise, and after that, the temperature preservation is performed for 0.5 h. Then the temperature is controlled to be 35±5° C., and 1220 mL solvent is removed by pressure reduction. After the removal is ended, the temperature is reduced to 20-25° C. at which the temperature preservation is performed for 3 h. After the temperature preservation and crystallization are ended, reducing pressure filtering is performed to obtain a wet product. It is subjected to reducing pressure drying in an oven at temperature of 35° C. for 12 h to obtain 124 g finished product of LCZ696, with a yield of 91% and a purity of 99.93%. The DSC and X-ray powder diffractive data of the obtained LCZ696 are matched with that reported by Novartis, the crystal form is consistent with that reported by Novartis, and the content data of respective components of the obtained LCZ696 refer to the following table.

|  | Content of Sacubitril | Content of Valsartan | Content of Sodium Ions | Water Content |
| --- | --- | --- | --- | --- |
| Theoretical Value | 42.8% | 45.3% | 7.2% | 4.7% |
| Measured Value | 42.6% | 45.1% | 7.4% | 4.9% |

EXAMPLE 12

Preparation of LCZ696 by the Sacubitril Dicyclohexylamine Salt

The Sacubitril dicyclohexylamine salt (84 g, 142 mmol) is dissolved into 900 mL acetonitrile, the temperature is raised to 60-65° C., after the solution is clear by stirring, the valsartan (63 g, 145 mmol) is added, then 47 g 36% Sodium hydroxide aqueous solution is added dropwise, the temperature is reduced to 50-55° C. at which the temperature preservation is performed for 2 h, then slow cooling is performed to 25-30° C., and temperature preservation and crystallization are performed for 3 h. After the crystallization is ended, filtration is performed to obtain a wet product. The wet product is subjected to reducing pressure drying in an oven at temperature of 35° C. for 12 h to obtain 110 g the finished product of LCZ696, with a yield of 81% and a purity of 99.92%. The DSC and X-ray powder diffractive data for the obtained LCZ696 are matched with that reported by Novartis, the crystal form is consistent with that reported by Novartis, and the content data of respective components of the obtained LCZ696 is seen in the following table.

|  | Content of Sacubitril | Content of Valsartan | Content of Sodium Ions | Water Content |
| --- | --- | --- | --- | --- |
| Theoretical Value | 42.8% | 45.3% | 7.2% | 4.7% |
| Measured Value | 42.7% | 45.2% | 7.2% | 4.9% |

What is claimed is:

1. A method for preparing a sacubitril/valsartan complex (LCZ696), comprising reacting a sacubitril dicyclohexylamine salt with valsartan in the presence of a sodium hydroxide aqueous solution in an organic solvent:

Sacubitril dicyclohexylamine salt valsartan

2. The preparing method according to claim 1, wherein the organic solvent is a mixed solvent of isopropyl acetate and acetone, a mixed solvent of isopropyl acetate and acetonitrile, or acetonitrile; and the preparing method comprises: dissolving sacubitril dicyclohexylamine salt in the organic solvent, adding valsartan into the organic solvent, raising a temperature of the organic solvent until the organic solvent is clear, adding the sodium hydroxide aqueous solution into the organic solvent dropwise, and performing crystallization.

3. The preparing method according to claim 1, wherein a molar ratio of the sacubitril dicyclohexylamine salt to valsartan is 1:0.95-1.10; and/or a molar ratio of the sacubitril dicyclohexylamine salt to sodium hydroxide is 1:2.95-3.10; and/or a mass percent concentration of the sodium hydroxide aqueous solution is 30%-40%.

4. The preparing method according to claim 2, wherein after the sodium hydroxide aqueous solution is added dropwise and before performing crystallization, and when the organic solvent is the mixed solvent of isopropyl acetate and acetone or the mixed solvent of isopropyl acetate and acetonitrile, operation step (i) is performed 2-3 times, wherein operation step (i) comprises: adding the isopropyl acetate dropwise and performing vacuum distillation.

5. The preparing method according to claim 2, wherein the temperature of the organic solvent is raised to 50-65° C. and the organic solvent is clear.

6. The preparing method according to claim 2, wherein crystallization is carried out at a temperature of 0-60° C.

7. The preparing method according to claim 1, wherein the sacubitril dicyclohexylamine salt is prepared by reacting sacubitril with dicyclohexylamine in ethyl acetate.

8. The preparing method according to claim 7, wherein the sacubitril dicyclohexylamine salt is prepared by dissolving sacubitril in ethyl acetate at 10-30° C., adding dicyclohexylamine dropwise, and cooling to 0-5° C. under a stirring condition to precipitate a solid.

9. The preparing method according to claim 8, wherein a molar ratio of sacubitril to dicyclohexylamine is 1:1.0-1.2.

10. The preparing method according to claim 8, wherein a molar ratio of sacubitril to the dicyclohexylamine is 1:1.05.

11. The preparing method according to claim 3, wherein the molar ratio of the sacubitril dicyclohexylamine salt to valsartan is 1:1.05.

12. The preparing method according to claim 3, wherein the molar ratio of the sacubitril dicyclohexylamine salt to sodium hydroxide is 1:3.05.

13. The preparing method according to claim 2, wherein after the sodium hydroxide aqueous solution is added dropwise and before performing crystallization, and when the organic solvent is the mixed solvent of isopropyl acetate and acetone or the mixed solvent of isopropyl acetate and acetonitrile, operation step (ii) is performed for 2-3 times, wherein operation step (ii) comprises: adding the isopropyl acetate dropwise within a temperature range of 40±3° C., performing temperature preservation at 40±3° C., and performing vacuum distillation in a temperature range of 35±5° C.

14. The preparing method according to claim 13, wherein a duration of the temperature preservation at 40±3° C. is 0.5-1h.

15. The preparing method according to claim 2, wherein after adding the sodium hydroxide aqueous solution dropwise and before performing crystallization, when the organic solvent is the acetonitrile, the temperature the organic solvent is kept at 50-55° C.

16. The preparing method according to claim 6, wherein crystallization is carried out at a temperature of 20-25° C.

* * * * *